Jan. 31, 1961 G. A. REID Plant Pat. 2,016
AZALEA PLANT
Filed Feb. 17, 1960
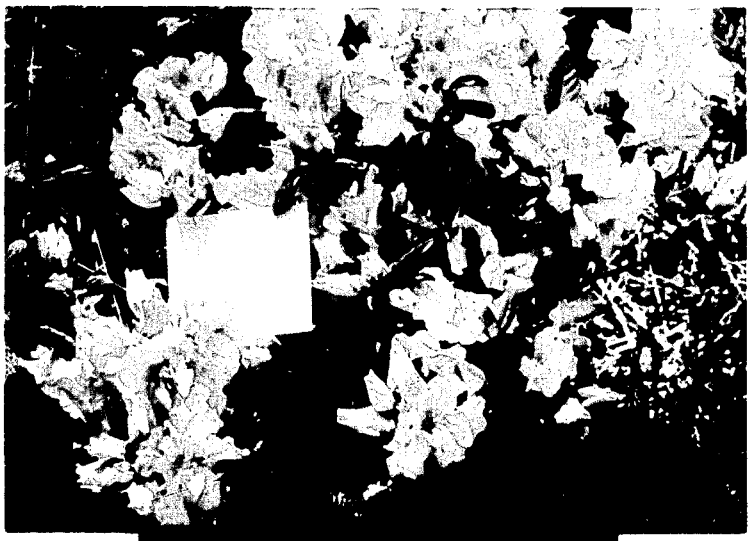
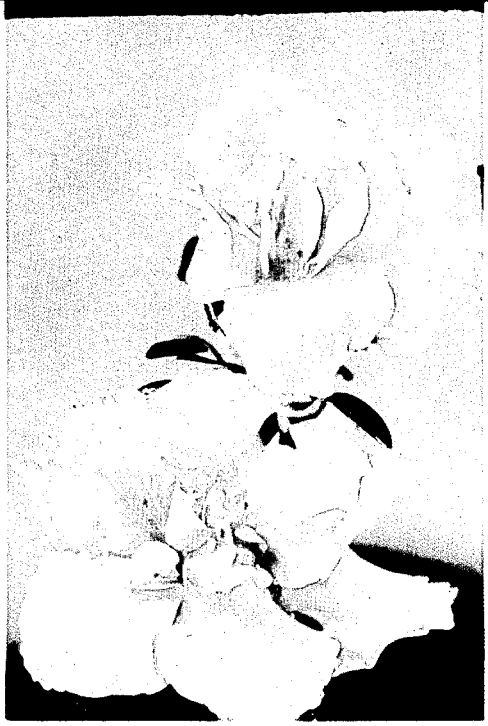
INVENTOR
George Albert Reid
BY Robb & Robb
ATTORNEYS United States Patent Office Plant Pat. 2,016
Patented Jan. 31, 1961

2,016

AZALEA PLANT

George Albert Reid, Linwood, N.J., assignor to Fischer Greenhouses, Linwood, N.J., a corporation of New Jersey Filed Feb. 17, 1960, Ser. No. 9,407

1 Claim. (Cl. 47—60)

The present invention relates to a new and distinct variety of azalea plant of the Indian azalea type, which was originated by me by crossing two unnamed and unpatented varieties on which no records of parentage were ever kept. These unnamed parent varieties were used in this breeding because of their good hardiness, it being my objective to try to produce a new azalea variety of the Indian azalea type and having good hardiness. So far as I am aware, Indian azalea type azaleas have never before been available in a hardy form and, accordingly, my achievement of this objective is something long desired, and is highly important from a commercial standpoint.

In achieving the aforementioned objective, other desirable improvements were obtained, as evidenced by the following combination of outstanding characteristics which differentiate my new variety from its parents, as well as from all other varieties of the Indian azalea type of which I am aware:

(1) Extremely good winter-hardiness (has withstood temperatures as low as −5° F. without injury to plant or flowers);

(2) Shiny foliage of Indian azalea-like form;

(3) Large, complicated semi-double flowers of Indian azalea-like form (usually averaging approximately 2¾ inches in diameter); and (4) A strong Purplish-Red general color tonality of the flowers.

Asexual reproduction of my new variety as performed by cuttings, at Linwood, New Jersey, shows that the foregoing characteristics and distinctions come true to form and are established and transmitted through succeeding propagations.

The accompanying drawing shows a typical specimen plant of my new variety, as well as typical specimen blooms on an enlarged scale, as depicted in color as nearly true as it is reasonably possible to make the same in a color illustration of this character.

The following is a detailed description of my new variety, with color terminology in accordance with Nickerson Color Fan, published by Munsell Color Company, Inc., of Baltimore, Maryland, except where general color terms of ordinary dictionary significance are obvious:

(Observations made from specimens grown in a greenhouse at Linwood, New Jersey.)

Propagation: Holds its distinguishing characteristics through succeeding propagations by cuttings.

*Plant*

Form: Bush; much branched; compact.

Habit: Medium vigorous.
Rooting habit: Uniform.
Foliage:
*Size.*—Large.
*Quantity.*—Normal.
*Color.*—New foliage: upper side—Moderate Yellow Green, Plate 5GY 5/6; under side—Brilliant Yellow Green, Plate 5GY 8/8. Old foliage: upper side—Moderate Olive Green, Plate 7.5GY 4/4; under side—Moderate Yellow Green, Plate 5GY 6/8.
*Shape.*—Oval pointed.
*Texture.*—Upper side—glossy; smooth. Under side—smooth.
*Margin.*—Shape—smooth edge.
*Aspect.*—Generally similar to Indian azalea type.
*Disease resistance.*—Good, as evidenced by the fact that no diseases have appeared over a period of several years, as compared with other varieties grown under the same cultural conditions in the same locality at Linwood, New Jersey.

*Flowers*

Borne: Several to stem; in irregular clusters; on strong stems of medium length.
Quantity of bloom: From free to abundant, both outdoors and in greenhouse.
Continuity: One season. Permanence—average.
Size: Large; about 2¾ inches in diameter.
Petalage:
*Number of petals under normal conditions.*—7 to 10.
*Color.*—Strong Purplish Red, Plate 10RP 4/12.
*Texture.*—Smooth.
*Appearance.*—Inside—from purplish pink to red. Outside—slightly lighter purplish pink to red.
*Shape.*—Slightly waved.
*Arrangement.*—Semi-double form; symmetrical.
General color tonality: Strong Purplish Red.
Bud: Color—strong Purplish Red, Plate 10RP 4/12.

*Reproductive organs*

Stamens: Color—pink, with black anthers.
Pollen: Color—white.
Styles: Color—pink.
Ovaries: Color—pale green.
General observations: The new variety more closely compares with the well-known variety "Jean Haerns" (unpatented) from the standpoint of growth habit, general color and aspect of the flowers and foliage, but the latter is more fully double and is not as hardy as the new variety. The combination of hardiness and Indian azalea-like double flowers and foliage is an exceedingly unique combination in azaleas.

I claim:

A new and distinct variety of azalea plant of the Indian azalea type substantially as herein shown and described, characterized particularly as to novelty by the unique combination of extremely good winter-hardiness, shiny green foliage of Indian azalea-like form, large, complicated, semi-double flowers of Indian azalea-like form, and a strong Purplish Red general color tonality of the flowers.

No references cited.